United States Patent [19]

Piasio et al.

[11] 4,305,924
[45] Dec. 15, 1981

[54] METHOD AND APPARATUS FOR PERFORMING IN VITRO CLINICAL DIAGNOSTIC TESTS USING A SOLID PHASE ASSAY SYSTEM

[75] Inventors: Roger N. Piasio, Yarmouth; David A. Perry, Portland; Pangal N. Nayak, Yarmouth, all of Me.

[73] Assignee: Ventrex Laboratories, Inc., Portland, Me.

[21] Appl. No.: 64,389

[22] Filed: Aug. 8, 1979

[51] Int. Cl.³ .................... G01N 33/56; G01N 33/58; G01T 1/00; B65D 71/00
[52] U.S. Cl. .................................. 424/1; 23/230 B; 422/61; 424/12; 435/7
[58] Field of Search ................. 424/1, 1.5, 12; 23/230 B; 422/61; 435/7

[56] References Cited

U.S. PATENT DOCUMENTS

| | | | |
|---|---|---|---|
| 3,932,141 | 1/1976 | Beall et al. | 23/230 B |
| 4,066,512 | 1/1978 | Lai et al. | 435/7 |
| 4,081,244 | 3/1978 | Polito et al. | 23/230.6 |
| 4,092,408 | 5/1978 | Litt | 424/1 |
| 4,111,754 | 9/1978 | Park | 435/7 |
| 4,116,638 | 9/1978 | Kenoff | 424/1 |
| 4,135,884 | 1/1979 | Shen | 23/230 B |
| 4,200,613 | 4/1980 | Alfrey et al. | 23/230 B |

OTHER PUBLICATIONS

Miles, L. E. et al., IAEA, 149 (1974).

*Primary Examiner*—Christine M. Nucker

[57] ABSTRACT

An improved method for performing an in vitro diagnostic test is provided. The method utilizes a solid phase device having a fixed component immobilized on its surface which is in contact with a fluid sample when inserted therein. The improvement resides in utilizing a receptacle, into which the device is inserted, having the same fixed component immobilized on the inner surface of the receptacle. The test is performed by placing a fluid sample, having a mobile component reactive with the fixed component, into the receptacle and in contact with the insert for a period of time and measuring a change which is a function of the concentration of the mobile component.

10 Claims, 6 Drawing Figures

METHOD AND APPARATUS FOR PERFORMING IN VITRO CLINICAL DIAGNOSTIC TESTS USING A SOLID PHASE ASSAY SYSTEM

BACKGROUND OF THE INVENTION

1. Field of the Invention

This invention relates to an improved method for conducting solid phase in vitro diagnostic assays.

2. Description of the Prior Art

In recent years, numerous techniques have been employed in the area of laboratory diagnostics to simplify operating procedures of existing methods and to provide new methods of improved speed, sensitivity, and accuracy. In particular, solid phase reactions have been especially valuable in simplifying the manipulations of prior art procedures and making possible procedures that could not be performed with conventional homogeneous phase reactions.

A solid phase reaction is generally carried out between one reactant, the fixed component, immobilized on the surface of an insoluble support matrix, and a second reactant, the mobile component, in solution. The reaction occurs when a molecule or a molecular arrangement of the mobile reactant, in the course of diffusion, collides with a molecule of the fixed reactant immobilized on the surface of the solid support matrix. The reaction may be a conventional chemical reaction, a binding of the mobile component by the fixed component as in an immunochemical reaction between an antigen and an antibody, or it may be a binding of the mobile component by the fixed component accompanied by chemical transformation of one of the components such as occurs in an enzyme-catalyzed reaction. Quantitative results are obtained by measuring the formation of products or disappearance of reactants as in the case of conventional and enzyme-catalyzed reactions, and in measuring the amount of the mobile component bound or the amount of mobile component unbound, in the case of an immunochemical reaction.

Any conventional chemical reaction or enzyme-catalyzed reaction resulting in a directly or indirectly measurable change can, in principle, be carried out by solid phase techniques. Directly measurable changes include changes in pH, light absorbance in the visible and ultraviolet regions or changes in fluorescence intensity. Indirect measurements can be made whenever the primary reactants or products are not readily measurable themselves by interposing the action of a reagent to carry out further reaction steps resulting in a measurable change and by the introduction of specific separation techniques. Such strategies may be employed alone or in combination, as is understood in the art.

Where the reaction consists solely of binding, in the absence of chemical change, techniques developed in the field of immunochemistry may be used to measure the extent of the reaction. Solid phase reactions are especially suited for immunochemical assays because the reactants in bound form may readily be removed from the solution by virtue of their attachment to the solid phase. Frequently, however, the components bound in an immunochemical reaction cannot be directly measured because they are indistinguishable by chemical methods from other substances commonly present in the same reaction mixture, so that the mere disappearance of a reactive component from solution or its accumulation on the solid phase cannot be measured directly. Therefore, additional steps must be taken in order to make a measurable change related to the amount of binding.

The variety of approaches taken by workers in the prior art can be grouped into two general categories. In the first of these, termed competitive or indirect immunoassays, the immobilized component is present in controlled amount and the mobile component present in unknown amount. To the unknown amount of mobile component is added a known amount of the same component which has been tagged by the addition of a measurable substituent which does not interfere with its immunochemical reactive properties. The tag may consist of a radioisotope, a chromophore, a fluorophor or an enzyme. The amount of tagged material bound immuno-chemically to the solid phase will depend upon the amount of untagged component in solution competing for the same binding sites. The more of the unknown present, the less will be the amount of tagged component bound.

In the second general method, termed the sandwich method or direct method, the solid phase containing an amount of immunochemically bound mobile component resulting from the first immunochemical reaction is subjected to the action of a reagent which can also bind immunochemically to the solid phase, but only at sites already occupied by the immunochemically bound mobile component. The reagent may be tagged, for example, as in the first method with a radioisotope, a fluorophor, a chromaphore or an enzyme. The amount of tagged reagent bound is a direct measure of the amount of mobile component bound, which, in turn, is a measure of the amount of mobile component initially present in the reaction mixture.

Where the tag is a radioisotope, the technique, whether competitive or noncompetitive, is termed a radioimmunoassay. When the tag is an enzyme, the assay is termed an enzyme-linked immunoassay. The amount of enzyme-tagged reactant is measured by any convenient method for measuring the activity of the enzyme used in the tag.

Other kinds of solid phase reactions of the ype generally described hereinabove are presented by way of example. The immunoradiometric assay for quantitative determination of an antigen is conducted by first reacting a known excess of labeled antibody with he unknown amount of antigen in a homogeneous phase reaction. Subsequently, immobilized antigen in excess amount is added in order to bind the unreacted soluble labeled antibody. The amount of unknown antigen is determined by measuring the difference between the total labeled antibody and the amount bound to the solid phase. The method gives direct quantitative results only with an univalent antigen, i.e., antigen which can only bind one molecule of antibody.

In such solid phase technology, the reagent or reagents used in the procedure are usually immobilized by being coated or bonded, either covalently or by adsorption to the solid phase material, which is then immersed in the sample to be tested. The manner of coupling such reagents to the solid phase material is known. See, for example, the disclosures in U.S. Pat. Nos. 3,652,761, 3,879,262 and 3,986,217.

A solid hase immunological assay system is disclosed in Miles et al., "Properties of Two-Site Immunoradiometric (Labelled Antibody) Assay Systems", IAEA, 149 (1974) in which solid-phase antibodies were bound to a tube wall by an immunoglobulin "arm". Polystyrene tubes were coated with non-immune guinea pig immunoglobulin (GP.IgG) or rabbit-anti (GP.IgG) (R-anti(GP.IgG)), and immunoglobulin "spacer arms" of various lengths were built up by alternative reactions with GP.IgG and R-anti (GP.IgG) leaving a final coat of the latter. Antibodies specific to glial fibrillary acidic protein (GP-anti(GFAP)) and to ferritin (GP-anti(ferritin)) were then immunologically bound to the solid phase. This placed specific solid-phase antibody at various distances from the matrix. Increasing "arm" length was shown to improve the precision of the dose-response variable.

U.S. Pat. No. 4,081,244, issued Mar. 28, 1978 to Polito et al. discloses a method for the preparation of an immunochemical composite comprising an antibody bound through a diamino spacer molecule to a finely divided polysaccharide matrix using a bifunctional coupling agent. The antibody coupled to the spacer may be either a primary or a secondary antibody, although the latter is preferred.

In U.S. Pat. No. 4,092,408 issued to Litt on May 30, 1978, a solid-phase radioimmunoassay method is disclosed in which anti-antibody is adsorbed on a solid surface and antibody is then bound to the anti-antibody. This immobilized antibody is then employed in a radioimmunoassay of antigen.

Examples of commonly used solid phase materials include, but are not limited to, glass or polymeric tubes which are coated with the reagent or reagents on their internal surfaces; coated polymeric inserts; coated polymeric sticks as disclosed in copending application Ser. No. 905,552 of Piasio et al., filed May 15, 1978 now U.S. Pat. No. 4,225,475; micro and macro beads formed of polymers and of glass; porous matrices; coated membranes; and tablets.

Immunochemical assays are highly useful in clinical research and diagnosis. They are highly specific, owing to the highly selective nature of antigen-antibody reactions. The antigen-antibody binding is very tight so that once the binding reaction has had an opportunity to occur, the limit of detectability is determined by the measurability with which the tag can be detected. Immunochemical assays are exceedingly versatile, owing to the fact that they can be used to measure specific substances selectively against a background of chemically similar substances. Because of these desirable attributes, there has been considerable interest in improving the ease of manipulation, sensitivity, accuracy, speed and applicability of immunochemical assays. The development of solid phase immunoassays has been one of the major advances in the field.

Among the advantages of solid phase systems is that the reaction product or products can be separated from the reaction solution with relative ease, i.e., by physically removing the solid phase material. This is in contrast with a non-solid phase or a homogeneous reaction, which typically results in a homogeneous solution which requires more complex separation techniques.

The introduction of solid phase technology has permitted the performance of novel procedures that were heretofore extremely difficult using free solution technology. An example of this is the sandwich assay technique described hereinabove. While a sandwich assay is theoretically possible in a homogeneous solution, it is not desirable for practical reasons. The most important aspect which makes such assays impractical is the separation of the first antigen-antibody complex from a homogeneous phase solution requires the use of sophisticated physical-chemical techniques, especially if the antigen is relatively small compared to the antibody and molecular weight differences between free antibody and complexed antibody are slight. In contrast, the separation procedure in a solid phase system is a matter of the utmost simplicity.

The earliest solid phase system devised were test tubes coated on the inside surface. Commercial examples of coated tube technology include the Immunotube$^{tm}$ system marketed by Smith Kline Instruments of Sunnyvale, California, and the Rianen TM system of New England Nuclear, North Billerica, Massachusetts, and the tubes described in U.S. Pat. No. 3,867,517 issued Feb. 18, 1975 to Ling. Although coated tube systems have proven useful for immunoassay purposes, they fail to exploit the full range of potential advantages offered by solid phase systems. A principle disadvantage is that the surface-to-volume ratio is relatively low and reaction kinetics may be further hindered by the fact that the reactive surfaces are located at the boundary of the solution volume, which may be relatively remote from the main body of the solution. Therefore, the average distance between mobile reactants and reactive surfaces is large.

The method of conducting in vitro diagnostic tests utilizing coated tubes is in widespread use. The disadvantages and defects of coated tubes are well known in the art. Many attempts have been made to improve on the performance of coated tubes with varying degrees of success. A description of several of these attempts will follow below. Some improvements have been made on the performance of coated tubes, but the search for better solid phase systems still continues. One improvement is he coated polymeric sticks as disclosed in copending application Ser. No. 905,552 now U.S. Pat. No. 4,225,475. Applicants have improved on the performance of these sticks by conducting the test in a receptacle which has the same coating as on the sticks. For example, a coated tube requires 70 minutes to reach 50% of equilibrium for digoxin assay. A coated stick, finned as described in application Ser. No. 905,552, on the other hand, requires 25 minutes. By utilizing such a coated finned stick and conducting the assay in a coated tube, 50% of equilibrium is reached in only 10 minutes—an improvement over both of the other two systems.

Attempts to improve on the performance of coated tubes have led to a variety of systems designed to increase the surface to volume ratio of the solid phase system. These methods have included providing highly convoluted surfaces, of finely divided material.

The SPAC$^{TM}$ system of Mallinckrodt Chemical Company is basically a coated tube system which exemplifies the strategy of providing a convoluted surface to increase surface area in the coated tube format. Additionally, the tubes are provided with a detachable lower section which may be batch coated to achieve greater uniformity from tube to tube.

A consequence of the batch immobilization on coated tube bottoms is that the outside as well as the insides of the tube become coated. This makes it difficult for the laboratory technician to wwork with the tubes without coming into contact with whatever materials are coated on their surface and valuable immunological reactants are wasted. The convoluted surface area is said to increase by hree to four times the amount of reactive surface available. However, the reactive surface remains at the periphery of the solution, which may be suboptimal geometry from the standpoint of the average diffusion distance from the solution to the reactive surface. Due to the complexity of the surface, difficulties in washing the surface free of contaminating substances may be encountered. As with coated tube systems in general, the SPAC$^{tm}$ system is likely to be sensitive to convection currents which can result in large errors as previously described. Convection may be reduced by carrying out the reaction in a constant temperature bath. However, this procedure presents additional equipment requirements for the clinical laboratory. For measurement of hapten antigens, the system is additionally suboptimal if the reaction is carried out at 37° C. according to the manufacturer's recommendation. It has been shown that increasing the temperature of a certain antibody-hapten reaction tends to enhance the rate of dissociation of the antibody-hapten complex relative to the rate of its formation. See Smith, T. W., and Skubitz, K. M., *Biochemistry* 14, 1496 (1975) and Keave, P. M., Walker, W. H. C., Gauldie, J. and Abraham, G. E., *Clinical Chemistry* 22, 70 (1976).

Various types of solid phase matrices designed to be inserted into the reaction fluid have been disclosed. A convoluted or sponge-like matrix designed to be inserted into the test solution is exemplified by U.S. Pat. No. 3,951,748, issued Apr. 20, 1976 to Devlin. This material offers relatively large surface areas but may be difficult to wash or drain thoroughly at the conclusion of the reaction. In addition, such systems may be limited in practice to the use of reactants and reagents which are readily eluted from the sponge matrix. More significantly, the sponge matrices tend to react extensively with only a portion of the reaction fluid, i.e., that portion which actually penetrates the pores of the matrix. Another solid phase matrix useful for assaying biologically active materials is disclosed in U.S. Pat. No. 4,066,512, issued Jan. 3, 1978 to Lai et al. This matrix comprises a microporous membrane, an inert proteinaceous material coated thereon, and a biologically active material immobilized onto this coating. This matrix can then be used for determining an unknown in a fluid sample.

A second type of insert, employing the strategy of forcing the reaction fluid to spread in a thin layer over the coated matrix surface, is disclosed in U.S. Pat. No. 3,826,619, issued July 30, 1974 to Bratu, et al., and U.S. Pat. No. 3,464,798, issued Sept. 2, 1969 to Kilthau. Both cases disclose a combination of a receptacle and closely-fitting insert matrix, so shaped as to sqeeze the reaction fluid into a thin layer between the container walls and the matrix surface. The insert matrix must fit the container with a close tolerance, and the volume of reaction fluid must be carefully controlled, since variations could adversely affect the reproducibility of the assay. The apparatus of Bratu is designed for use in a direct immunochemical test that is qualitative only. Because the reaction solution is forced into a thin film by the insert, the reaction volume must necessarily be small and Bratu in fact discloses that the type of assay contemplated is designed for small volumes of undiluted serum. One of the pitfalls of this type of assay is that errors in the rates of antigen-antibody reactions may be caused by variations in the pH of undiluted serum, which may vary between pH 6 and pH 9 in clinical samples. The pH may be controlled by the addition of a buffer, but buffer salt concentrations greater than 0.1 M tend to dissociate antigen-antibody complexes. Therefore, an excess volume of low ionic strength buffer must be used to control pH accurately, and this may expand reaction volume to an unacceptable amount. Error due to the pH may be tolerated in a qualitative assay such as disclosed by Bratu et al., especially in samples relatively rich in concentration of unknown, but not in the quantitative assays for which the present invention is designed. Where diluting by buffer is required, a low concentration of unknown may be diluted below the level of detection, leading to false negative results with the Bratu or Kilthau device. A false negative result is one in which no unknown is detected when some should have been detected. One embodiment of the Bratu insert is an insert having four fins. Its use is disclosed for qualitative analysis where larger quantities of serum are available, but there is no suggestion of any different mode of operation from the thin film mode utilized with the rounded or conical version. The devices disclosed in U.S. Pat. No. 3,826,619 have not, so far is known, been commercially exploited.

An example of an insert which utilizes the "intimate contact" principle of Bratu and Kilthau, but is apparently used quantitatively, is disclosed in U.S. Pat. No. 4,135,884 issued Jan. 23, 1979 to Shen and represented by the "Gamma Stick TM [$^{125}$I] T$_3$ Uptake Kit" of Alpha Gamma Labs, Inc., Sierra Madre, California. This insert has four flutes which are coated with an antigen or antibody and inserted into a test tube containing the unknown sample, in intimate contact with the sample.

A third type of solid phase insert matrix is represented by the StiQ TM assay of International Diagnostic Technology Corporation, Santra Clara, California, designed to exploit a solid phase assay disclosed in U.S. Pat. No. 4,020,151, issued Apr. 26, 1977 to Bolz, et al. In this system, a disc shaped, uncoated insert maxtrix of material capable of adsorbing proteins from serum is provided. In this system, the limitations are not only due to surface-to-volume ratio or geometric considerations but are mainly due to problems associated with the initial adsorption step, such as the presence of interfering substances and the difficulty of obtaining measurable adsorption components present in low concentration.

Another example of an attempt to improve surface-to-volume ratio by reducing reaction volume is disclosed by Friedel, R. and Dwenger, A., *Clin Chem.* 21 967 (1975). In this system, capillary tubes are coated on the inside with a specific adsorbant and the reaction mixture is introduced into the lumen of the capillary tube.

A further example of such a device is disclosed in U.S. Pat. No. 4,111,754, issued Sept. 5, 1978 to Park which relates to a solid phase matrix having a cylindrical supporting surface with inwardly directing protuberations. The spacing between the protuberations is such that a liquid sample will be retained within the matrix by capillary action so that the sample can only be removed from the matrix by addition of another fluid on top of the matrix to build up a hydrostatic pressure head sufficient to overcome the capillary attraction. A further example of the continuing prior art trend toward maximizing surface to volume ratio and capillary devices is shown by U.S. Pat. No. 4,116,638 issued Sept. 26, 1978 to Kenoff. The Kenoff device consists of a bundle of capillary tubes contained in a holder designed to be inserted into a sample contained in a test tube.

One system which affords a high surface area for overall volume is the coated micro glass bead system as, for example, the Immo Phase TM system of Corning Glass Works. This system exemplifies the use of finely divided particles. It provides a high coated surface area with a correspondingly high reaction rate. Due to settling of the particles during the reaction, optimization of test systems of this kind require that the test tubes in which they are placed during reaction be capped and mixed vertically during reaction to insure that all surfaces come in contact with the reactants. Further, the use of particles necessitates multiple centrifugations and washings to completely separate the immobilized product from the solution.

Another example of a system which affords high surface area for over-all volume is the coated macro bead as disclosed in U.S. Pat. No. 3,932,141, issued Jan. 13, 1976, to Beall et al. and represented by the AUSRIA$^{tm}$ II-125 and AUSAB$^{tm}$ assays of Abbott Laboratories, North Chicago, Ill. This bead is designed so that a minimal amount of sample is required. It appears that the sample forms a thin film around the bead and as such would have the same deficiencies as described above for the Bratu device. This bead appears to be only useful for qualitative analysis and not for quantitative analysis.

Other examples of solid phase matrices, which alleviate many of the deficiencies of the prior art, are disclosed in copending patent application Ser. No. 805,431, filed June 10, 1977 of Piasio et al. now U.S. Pat. No. 4,197,287 and copending patent application Ser. No. 905,552 of Piasio et al., filed May 15, 1978 now U.S. Pat. No. 4,225,475. Application Ser. No. 805,431 discloses a water-insoluble solid phase matrix for insertion into a reaction vessel which comprises an elongated annular support surface and a plurality of water-insoluble fins projecting from the support surface. An antigen or an antibody capable of reacting with a mobile component in a liquid sample to be assayed is immobilized on the interior of the annular surface and on each of the fin surfaces. Application Ser. No. 905,552 discloses another water-insoluble solid phase matrix for insertion into a reaction vessel which comprises a handle having a plurality of essentially smooth curved or planar surfaces attached thereto which extend throughout the liquid sample being assayed. An antigen or an antibody is immobilized on the curved or planar surfaces which reacts with a mobile component in the liquid sample.

Prior attempts to improve on coated tubes as a solid state reaction matrix have frequently resulted in some improvement in reaction rate or the time necessary to carry out a measurable reaction. Such improvement has often been accomplished by concomitant increase in manipulative difficulty, or loss of flexibility.

SUMMARY OF THE INVENTION

These drawbacks and disadvantages of the prior art have been alleviated by the present invention. In accordance with the present invention, an improved method is provided for conducting an in vitro diagnostic test in which one or more reactants, each termed a fixed component, is attached to solid phase matrix and one or more other reactants, each termed a mobile component, is dispersed in a liquid medium in which the matrix is brought into contact therewith. In particular, a fixed reactant is attached to an insert which may be immersed in the liquid. The improvement in the method comprises conducting the test in a receptacle to which the same fixed reactant has been attached.

The shape of the insert is designed to provide an optimal surface-to-volume ratio and a shorter average diffusion distance between the mobile reactants in solution and the fixed reactants on the solid phase surfaces of the insert and receptacle, and also to permit the liquid to drain freely from the insert and receptacle when the liquid is poured therefrom. The insert of the present invention may comprise any insertable solid phase matrix known in the art, e.g. beads, membranes, tablets or polymeric inserts. However, it is preferred to use a stick as described in copending application Ser. No. 905,552 having at least nine fins. This nine-fin stick comprises a plurality of essentially smooth or curved planar surfaces attached to a supporting member which are of a size and shape and are arranged in such a fashion with respect to the reaction fluid that the insertion of the stick in the fluid reduces the average diffusion distance of the mobile component molecules to the stick surface compared to the average diffusion distance to the inner surface of the receptacle when no insert is present. The actual shape of a given finned stick may, but need not, be designed to conform to the size and shape of the receptacle into which it is placed. However, the finned stick matrix must extend substantially through the depth of the fluid sample in the vessel. In some systems, these finned stick matrix surfaces preferably extend above the surface of the reaction fluid thereby producing an essentially constant geometric relationship through the depth of the reaction fluid and further providing that the same geometric relationship will exist regardless of any changes in the fluid volume.

The receptacle, according to this invention, is also a solid phase matrix into which the insert is placed. Through the use of this receptacle, preferably a test tube, the solid phase area is increased, thereby increasing the surface-to-volume ratio. Moreover, when the preferred nine fin stick insert is used, the coated receptable aids in a lower average diffusion distance of the mobile component to the immobile component. In the preferred embodiment, the tube has one or more indentations which hold the nine fin stick insert within the tube when draining the fluid therefrom. The solid phase matrix on the receptacle must extend substantially throughout the depth of the fluid sample in the vessel, regardless of the type of insert used. Also, in some systems, the solid phase matrix preferrably extends above the surface of the reaction fluid, thereby producing essentially constant geometric relationship throughout the depth of the reaction fluid and further providing that the same geometric relationship will exist, regardless of any changes in the fluid volume.

In the preferred embodiment of the present invention, where a coated tube and coated nine fin insertables matrix are employed together, an immunological spacer consisting of immunoglobulin G (IgG) is adsorbed on the surfaces of both the insertable matrix and the receptacle. An anti-antibody is then immunologically bound to the IgG. The matrix can then be used as a solid phase anti-antibody in any immunological antibody-antigen assay employing a primary antibody. Alternatively, the solid phase anti-antibody could be allowed to react with a solution containing only primary antibody and the resulting solid phase antibody used in a direct or indirect immunoassay for antigen.

Advantages of the invention include the minimization of timing errors in starting and stopping a reaction, high reaction rates permitting faster tests, reduction of volumetric transfer errors, reduced error of measurement at a given level of sensitivity and ease in manipulation. The high reaction rate with the preferred embodiment permits immunochemical assays to be conducted at room temperature or lower, which may be advantageous over higher temperatures. The high reaction rates of the present invention now make it possible to use reagents in the diagnostic tests, the use of which was considered marginal when the tests were performed with the methods of the prior art. The high reaction rates allow for the shortening of the test. A significant advantage of the present invention is the faster rate, shorter time and greater percentage of binding which occur when a coated insert assay is performed in a receptacle having the same coating. This advantage is even more significant when an enzyme is assayed or used as a label in an immunoassay. By conducting a coated insert assay in a coated receptacle, the amount of non-specific binding, i.e. binding of an antigen at a site other than the appropriate antibody, is minimized, thereby increasing the precision of the assay. The device is expected to provide ease of manufacture, consequently economy and uniformity of product.

DESCRIPTION OF THE PREFERRED EMBODIMENTS

Figures 1, 2:
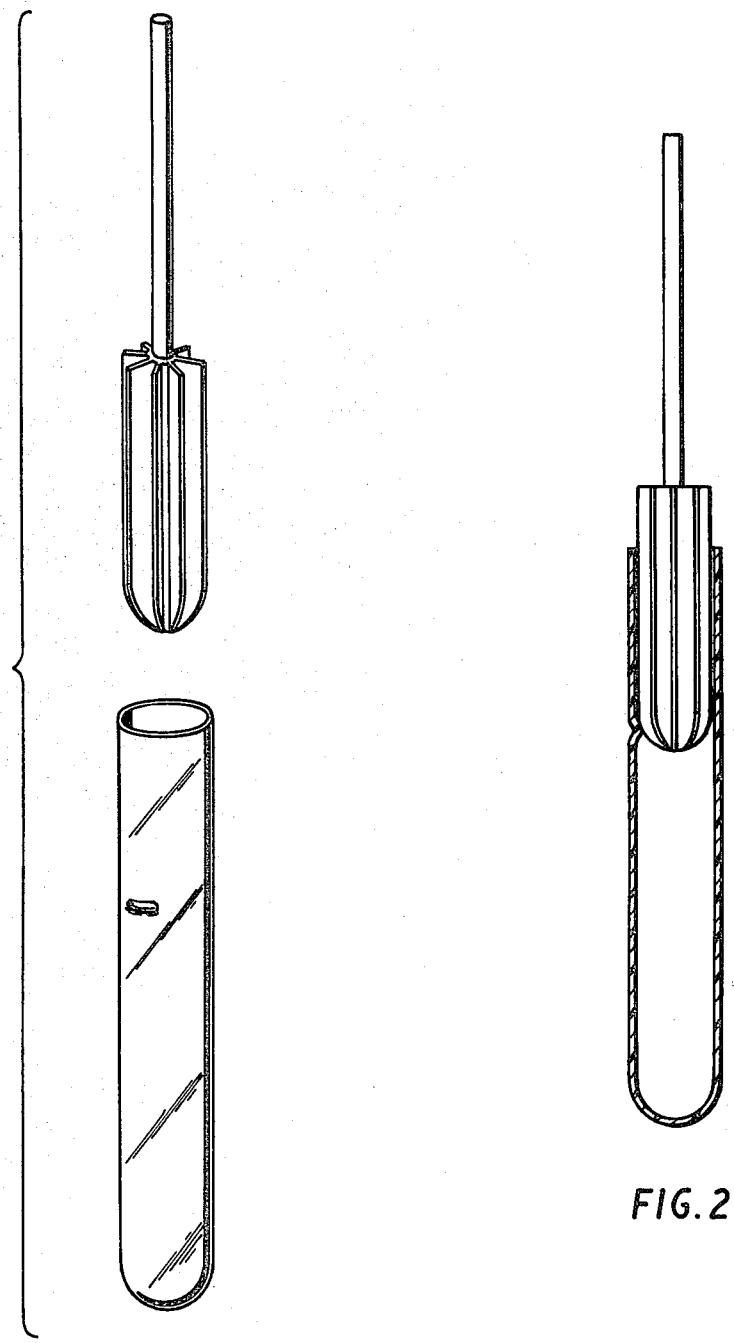
FIG. 1 illustrates the preferred embodiment in accordance with the invention.
FIG. 2 is a cross-section of the test tube as illustrated in FIG. 1, showing the indentations in the tube restricting the entry of the stick.

In the method of the present invention, a solid phase reaction is carried out in a receptacle using one or more of the reaction components bound to the surface of an insert which is placed into the reaction fluid in the receptacle. The improvement of the present invention over the prior art solid phase insert assays is that the assay is conducted in a receptacle having the same coating, i.e. components bound to the surface, as the insert. Preferably, the reaction components bound to these surfaces are bound by means of an immunological spacer and an anti-antibody. For purposes of illustration, reactions carried out in test tubes are described and a stick as described in copending application Ser. No. 905,552 having at least nine fins and designed to be inserted into the test tubes are discussed. Preferably, the test tube has one or more indentations in it which allow for easy insertion of the stick, but which will hold the stick within the tube when the liquid is drained out. The reaction is readily initiated by adding the mobile component into the tube which contains a solid phase coating and inserting the solid phase coated stick into the tube. The reaction may be terminated by draining the fluid from the tube. After the reaction has been terminated, the tube and stick may be placed in a radioactivity counting chamber or other measurement device, depending upon the nature of the assay method.

The solid phase reaction kinetics are more complex than for homogeneous phase reaction. A detailed theoretical basis for optimizing insert design is not available. However, certain basic considerations of a general nature can be taken into account. The total surface area in contact with the solution is one of several important factors. The larger the area, the greater the amount of fixed component which may be present in the reaction. Increasing the effective concentration of either component will generally increase the overall reaction rate. Since the amount of the fixed component is determined by, among other factors, the area of solid phase, the reaction rate should vary directly with the surface-to-volume ratio. An increased surface-to-volume ratio is achieved in the present invention by conducting a coated insert assay in a receptacle having the same coating, i.e. both the insert and the receptacle have the same fixed component. A second factor possibly affecting the reaction rate is the average diffusion distance between the mobile and fixed reactants. As is evident, "average diffusion distance" means the sum of the distances each of the mobile component molecules must diffuse, by the shortest possible path to reach a fixed component, divided by the total number of such molecules. By using a coated receptacle with the coated insert assay, the average diffusion distance of mobile phase molecules to a fixed component adhering to the surface elements of the receptacle and insert is reduced. Transfer of mobile reactants to the reactant surfaces is thought to be facilitated by decreasing the average distance between mobile reactants and the reactive surfaces. Increased reaction rates have been observed by conducting the coated insert assay in a coated receptacle according to the present invention. Also, reactions approach equilibrium sooner using the method of the present invention than with either a coated tube assay or a coated insert assay.

In performing an immunoassay, the ideal situation is to reach equilibrium. As equilibrium is approached, the accuracy, precision and reproducibility of the assay is improved. Thus, the faster equilibrium is reached, the better the assay. The increased binding capacity as a result of utilizing a coated receptacle in the coated insert assay causes the reaction to reach equilibrium sooner. This provides for better precision which is reflected in the coefficient of variation. It was observed that the assays conducted according to the present invention appear to show a greater consistency in the coefficient of variation than for the tube assay or the stick assay.

Additional advantages are provided by the present invention. The provision of an increased total surface area makes it possible to conduct quantitative determinations over a wider range of mobile reactant concentrations due to enhanced detectability at the lower end of the concentration range and increased binding capacity, such that proportionate response is possible at higher concentrations of the mobile reactant. Additionally, the present invention of performing the coated insert assay in a receptacle having the same coating may be used to carry out direct, or sandwich assays of a quantitative sort. For this application, the increased binding capacity available when the coated insert assay is performed in a receptacle having the same coating is desirable in order to immobilize materials over the entire range of potential concentrations, and not merely enough to provide a simple "yes-no" test. See, e.g., Bratu et al. U.S. Pat. No. 3,826,619. For sandwich type immunoassays, the range of antigen concentrations which may be measured quantitatively using a preferred embodiment of the present invention is very large. The applicable range of the assay is determined by a complex interaction involving the matrix geometry, the amount of distribution of the antibody bound to the surface of the insert and the receptacle, and the method employed. The size and shape of the insertable matrix affects the kinetics of the immunochemical reaction, which in turn affects the amount of immobilized component necessary to provide a differential response with the amount of mobile component to be measured. Additionally, the stability of the bound component and the uniformity of its distribution are parameters affecting the design of the coated matrix. Advantageous results are obtained in a competition immunoassay by the present invention of performing a coated insert assay in a receptacle having the same coating in that control of all significant factors affecting sensitivity range and reproducibility is permitted. Additionally, the process of the present invention employs a reaction volume sufficiently large to permit a serum sample to be diluted with a buffer to control the pH and reduce errors due to variations of sample pH, or other factors such as protein concentration, and to provide constant volume, if necessary, from sample to sample.

In a competitive binding assay, one factor which affects the precision or performance of the assay is non-specific binding. For example, non-specific binding is the binding of antigen to the solid phase matrix other than at the appropriate antibody. This non-specific binding can lower the precision of the assay. This decrease in precision is particularly a problem when the fluid sample contains a high concentration of antigen. At this point, a relative higher percentage of labeled antigen is being non-specifically bound yielding a lower concentration reading of the antigen. It is important to control or at least to minimize the impact of non-specific binding. The amount of non-specific binding from one unknown sample to another is not predictable. It appears that several factors may influence non-specific binding. For example, in serum samples, one factor which may influence non-specific binding is serum proteins. These factors may vary from one unknown sample to the next. This variation results in a variation in non-specific binding for each sample. Thus, one sample may have a higher non-specific binding than another sample has. This difference would not be discernible in the test procedure. As a result, the accuracy and precision of the test will be lower. Therefore, it is important to minimize non-specific binding. In conducting an assay with a coated insert alone, a disproportionate amount of non-specific binding, i.e. non-specific binding relative to specific binding, occurs on the uncoated receptacle. By coating the receptacle, it was found that the amount available for specific binding is increased. This results in a decrease in the non-specific binding of the coated receptacle relative to its specific binding capability. This helps to minimize the effect of non-specific binding.

A sandwich immunoassay is a direct assay of the antigen or antibody present in the fluid sample. The ability to bind antigen, for example, is dependent on several factors, one of which is the concentration of solid phase antibody. Similarly, the amount of labeled antibody bound is dependent on the antigen previously bound. The amount of labeled antibody bound is critical for the detection of antigen. The greater the binding capacity, the greater the accuracy of the assay. Thus, the increased binding capacity as the result of conducting the coated insert assay in a receptacle having the same coating provides for greater accuracy in the detection of antigen in the fluid sample.

In both competitive and sandwich immunochemical assays, the length of time required to carry out the assays is dependent upon the rate at which the reaction approaches equilibrium. Reactions carried out by the method of the present invention approach equilibrium faster than the conventional coated tube assays or the various coated insert assays of the prior art and may therefore be carried out in a shorter time. Furthermore, the method of the present invention provides a very effective and precise means of starting and stopping reactions. This advantage becomes significant when it is necessary to carry out a large number of assays at one time. In such cases, the time spent in the manipulations of starting and stopping the reactions is reduced to a minimum and can be more precisely controlled for all samples of a series.

An additional advantage which stems from the enhanced reaction rate and increased capacity of the method of the present invention is that the same device can be used for both sandwich and competitive assays. This device allows the performance of a functional immunoassay in less overall time than previously possible in the prior art. The overall time is defined as the time interval between starting the assay and measuring the results. When used in a quantitative competitive assay, the device provides a wide range of proportionate response as described previously and demonstrated in the examples.

It will be appreciated that design of a properly functional solid phase matrix requires attention to all aspects and variables affecting the reaction to be conducted. In addition to providing a structural basis for enhanced reaction rates, operating convenience, minimized background interference and all the other advantages of the present invention, it is important to provide a coated surface having immobilized reactant distributed therein in such a manner that its reactivity is maximum. The immobilized component should be distributed as uniformly as possible over the surface. Gaps in the coating, which may be caused, for example, by an air bubble lodged on the matrix surface during the coating step, must be avoided. The immobilized reactant molecules must be exposed on the matrix surface, not buried in excess reactant or other carrier matter. Preferably, the immobilized reactant should be bound to the matrix sufficiently strongly that no appreciable amount of reactant becomes desorbed, or otherwise removed during the incubation or washing steps of the reaction. In accordance with the preferred embodiment, the reaction component is accessible because it is immunologically bound to an anti-antibody which in turn is immunologically bound to an immunological spacer which is adsorbed to the surfaces of the matrices.

In accordance with the present invention, a coated insert assay is conducted in a receptacle having the same coating. Preferably, a coated test tube is utilized as the receptacle, but coated beakers and the like could also be used. The insert may be any conventional solid phase matrix which can be inserted into the receptacle. Examples of suitable matrices include: polymeric inserts, micro beads, macro beads, coated membranes, tablets, close-fitting inserts as described by Bratu et al., Kilthau, or Shen or sticks as disclosed in copending application Ser. No. 905,552. Although any type of coated insert may be utilized, it is preferred to use a stick having at least nine fins as described in copending application Ser. No. 905,552, incorporated herein by reference. The preferred embodiment of the present invention consisting of a coated tube and coated stick is shown in FIG. 1.

The preferred tube is any commercially available 12×75 mm polystyrene test tube, with a round or square bottom, which has been modified. The test tube has been modified by placing one or more indentations on the outer surface of the tube such that the inner surface has a "lip". The "lip" is illustrated in FIG. 2. The size of this "lip" is such that the preferred insert will rest on it and not fall into the lower portion of the tube until it is pushed past the "lip" and into the lower region of the tube. Similarly, the preferred insert is held within the tube by this "lip" when the tube is inverted so that the fluid is drained from the tube. This provides for easy drainage of the reaction fluid by decantation and washing of the coated tube and the preferred coated, nine fin stick. The indentations in the tube are made as follows. The test tube is rotated and while being rotated is brought into contact with a heated arc. This heated arc softens the polystyrene and forces in the heated portion resulting in the "lip". The preferred insert is a stick having at least nine fins which is made in accordance with copending application Ser. No. 905,552.

The tube and insert may be coated using any method known in the art. In the preferred embodiment, an immunological spacer is adsorbed onto the inner surface of the tube and onto the surface of the insert which is in contact with the fluid sample when inserted therein. An anti-antibody is then immunologically bound to said spacer. The tube and insert coated in this manner can then be used as a solid phase anti-antibody in any immunological antibody-antigen assay employing a primary antibody. Alternatively, an antibody could be immunologically bound to the solid phase anti-antibody. This solid phase antibody could then be used in a direct or indirect ummunoassay for antigen.

A more complete appreciation of the invention will be realized by reference to the following specific examples. These examples are not intended to limit the invention disclosed herein except to the extent to which limitations appear in the appended claims. In the following examples, all radioactivity counts were measured at 48% efficiency.

EXAMPLE 1

This example describes the immobilizing of antibodies to a tube and a preferred nine fin stick.

The antibodies and anti-antibodies are prepared in the conventional manner. Thus, an antibody may be prepared by injecting an antigen into a rabbit. Rabbit immunoglobulin G (IgG) is injected into a second animal, e.g., a goat, to prepare goat antirabbit and anti-antibody. This anti-antibody will bind any antibody produced in rabbits. In this particular example, rabbit immunoglobulin G will be the most suitable immunological spacer.

12×75 mm commercially available polystyrene tubes were modified as described above. These tubes and 9-fin sticks as described in copending application Ser. No. 905,552 were coated with 1.4 ml of Rivanol fractionated rabbit IgG containing 10-20 ug of IgG/ml. Coating was performed in the standard fashion employing a buffer of pH 7.5 containing 0.01 M phosphate, 0.15 M NaCl and 1 mg/ml NaN$_3$. The coating reaction was performed for 18 hours at 5°-9° C. The tubes and sticks were then washed.

Goat antirabbit anti-antibody was then immunologically bound to the IgG coated tubes and sticks. 10 ug of goat IgG containing 10-30% anti-antibody/1.4 ml of the same buffer was used for this step which was performed for a minimum of 18 hours at room temperature. The tubes and sticks were then washed and air dried.

The anti-antibody coated tubes and sticks were then ready to immunologically bind specific antibody produced in rabbits. For example, rabbit anti-digoxin was bound to the anti-antibody in a similar manner. The anti-digoxin in buffer was immunologically reacted with the anti-antibody coated tubes and sticks for 24 hours at room temperature. The tubes and sticks were washed and air dried. They were then ready to be used in an immunoassay to determine the amount of digoxin in the fluid sample. The final coating procedure could utilize any rabbit antibody.

EXAMPLE 2

This example demonstrates that performing an assay with the preferred coated stick in a tube having the same coating has better reaction kinetics than a coated tube assay alone or a comparable coated stick assay alone.

Tubes and 9-fin sticks were coated with IgG, anti-antibody and anti-digoxin as described in Example 1. Digoxin Buffered Tracer Reagent was prepared by adding $^{125}$I-labeled Digoxin to phosphate-buffered saline (PBS) composed of 0.006 M NaH$_2$PO$_4$, 0.024 M K$_2$HPO$_4$, 0.15 M NaCl and 0.1% bovine serum albumin at pH 7.4. Sufficient labeled Digoxin was added to the buffer to provide 20,761 counts per minute (cpm) per ml of buffer.

1.0 ml of the Tracer Reagent was added to coated and uncoated tubes and vortexed for 1-2 seconds. Coated sticks were placed in half of the coated tubes and in all of the uncoated tubes. Uncoated sticks were placed in the other half of the coated tubes. All sticks were placed in the tubes so that they rested on the "lip". All sticks were then pushed into the tubes as rapidly as possible. The coated tubes, coated sticks and coated tube-coated stick combinations were incubated for various lengths of time at room temperature. After each interval, the tubes were inverted and gently shaken to drain the tubes of the radioactive Tracer Reagent. The tubes were then rinsed twice with approximately 2.5 ml of 0.01% Triton and finally counted in a gamma scintillation counter. The incubations were stopped at 15 minute intervals throughout a three hour period.

Figure 3:
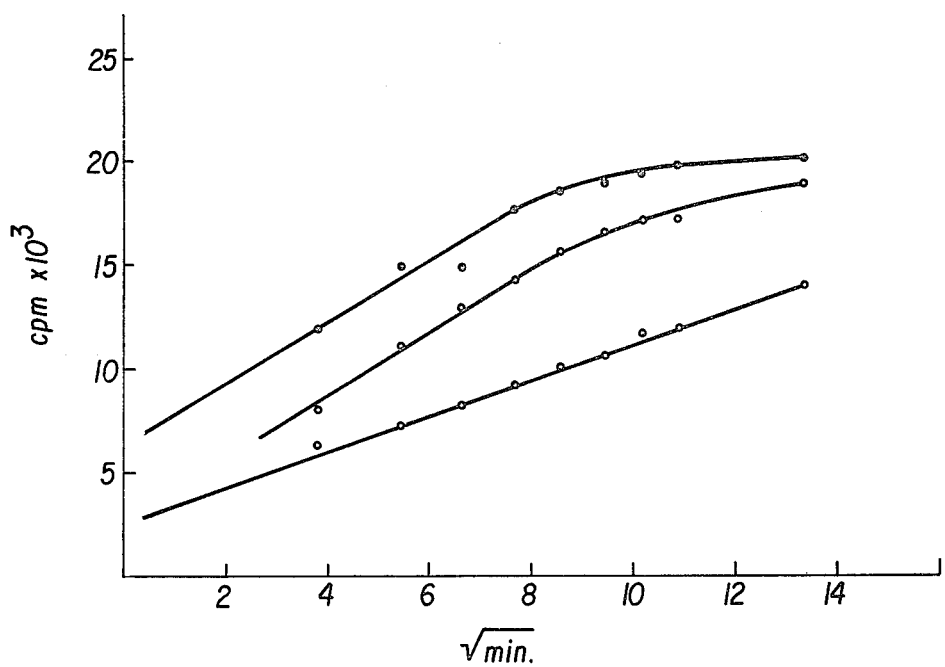

The results are plotted in FIG. 3. It can be seen that the coated tube-coated stick combination was able to bind a greater amount of antigen throughout the course of the reaction at room temperature. The following table shows the time which was required to reach a particular percent of equilibrium.

TABLE 1

| | Time (min.) | | |
|---|---|---|---|
| % of Equilibrium | Coated Tube | Coated Stick | Coated Tube-Coated Stick |
| 25 | 8 | 3 | <2 |
| 50 | 70 | 25 | 10 |
| 75 | 220 | 70 | 35 |
| 90 | 400 | 100 | 75 |

This shows that the preferred coated stick assay conducted in a coated tube having the same coating is able to reach equilibrium in less time than either the coated tube assay or the coated stick assay.

EXAMPLE 3

This example demonstrates the response of the preferred coated stick assay conducted in a coated tube to increasing concentration of antigen in a competitive assay. Two separate experiments were conducted. One experiment was conducted using digoxin as the antigen and a second was conducted using thyroxin (T$_4$) as the antigen. The basic procedure for assaying digoxin or T$_4$ is as follows:

1. Label plastic tubes (supplied) for every standard, control and patient sample to be assayed.
2. Pipet 100 microliters (0.1 ml) of standard, control or patient sample into the appropriate tube.
3. Add 1.0 ml Digoxin Buffered Tracer Reagent to each tube.
4. Vortex for 1-2 seconds.
5. Place on Ventre/Sep TM Digoxin Antibody Stick in each tube so that it rests on the notch. Press all sticks into tubes as rapidly as possible.
6. Incubate for 15 minutes at room temperature.
7. Invert tubes and gently shake up and down to drain into radioactive waste container; blot on an absorbent pad.
8. Rinse each tube with approximately 2.5 ml 0.01% Triton. Repeat Step 7 (above).
9. Repeat Step 8 (above).
10. Place tubes in gamma scintillation counter and count.

The tracer reagent for digoxin is the same as used in Example 2. The tracer reagent for T$_4$ was prepared by adding merthiolate (for releasing T$_4$ from serum protein) and $^{125}$I-labeled thyroxin to PBS. In this example, sufficient labeled digoxin was added to the buffer to yield approximately 24,000 cpm/ml of buffer. Similarly, sufficient labeled thyroxin was added to the buffer to provide approximately 30,000 cpm/ml of buffer. For the digoxin experiment, 100 microliters of standard having a concentration of 0, 0.5, 1, 2, or 4 nanograms per ml were added to the appropriate tube and the remainder of the experiment followed as listed above. For the thyroxin experiment, 50 microliters of standard containing 0, 30, 60, 120 or 240 nanograms per ml of thyroxin were added to the appropriate tube. Similarly, three commercially supplied controls were added to appropriate tubes. For thyroxin, the incubation was conducted for 30 minutes at room temperature; otherwise, the remainder of the conditions were the same as listed substituting Thyroxin Buffered Tracer Reagent and Thyroxin Antibody Sticks where appropriate.

Figure 5:
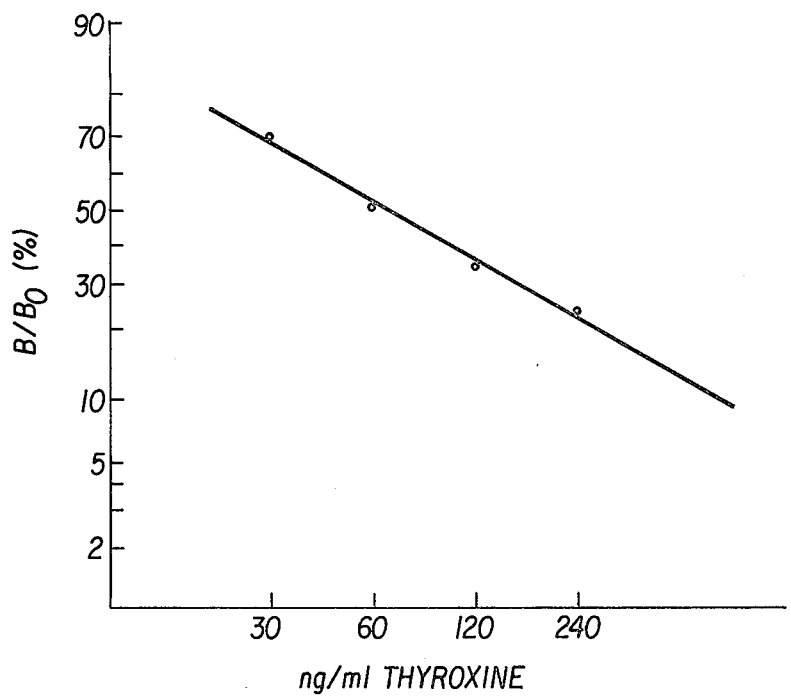
FIGS. 3-6 are graphs.
Figure 4:
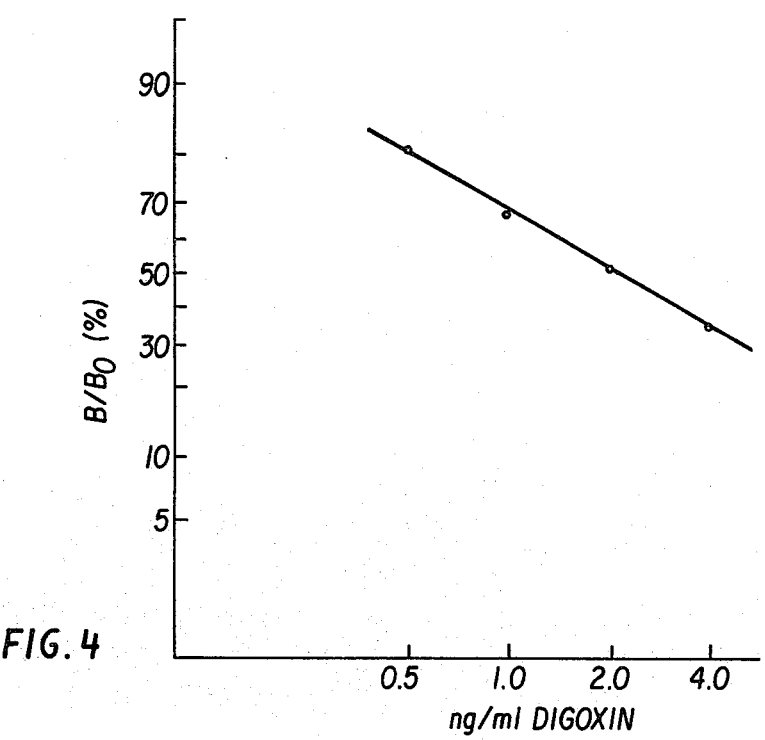

The results of these experiments are shown in FIGS. 4 and 5. The nanograms/ml is plotted on the horizontal axis using a log scale. The percent of the amount of label bound for any given amount of standard digoxin or T$_4$ compared to the amount of label bound for 0 ng/ml of standard digoxin or T$_4$ (B/B$_o$) is plotted on the vertical axis using a percentage scale. These figures show that the amount of label which is bound decreases in a linear relationship with increasing concentration of thyroxin or digoxin orginally present in the assaying medium. The B$_{50}$ for digoxin was 2.1 ng/ml and the B$_{50}$ for thyroxin was 68 ng/ml.

The controls utilized for the T$_4$ experiment were controls supplied by DADE TM division of American Hospital Supply Corporation, Miami, Fla. The controls were assayed as described above and the B/B$_o$ was calculated. The experiment concentration for T$_4$ was then determined by reading off the appropriate graph. The theoretical and experimental values in ng/ml are shown in the following Table.

TABLE 2

| Control | Theoretical | Experimental |
|---------|-------------|--------------|
| 1       | 25          | 19           |
| 2       | 84          | 81           |

TABLE 2-continued

| Control | Theoretical | Experimental |
|---------|-------------|--------------|
| 3       | 160         | 145          |

The experimental values correspond closely with the theoretical values with the exception of number 3 which produced a low result.

EXAMPLE 4

This example illustrates the assay procedure for Ferritin which is a sandwich assay. Antibody to Ferritin is coated on the sticks and tubes following the procedure as described in Example 1. The procedure for assaying Ferritin is as follows:

1. Label plastic tubes (supplied) for every standard, control and patient sample to be assayed.
2. Pipet 50 microliters (0.05 ml) of standard, control or patient sample into the appropriate tube.
3. Add 1.0 ml Assay Buffer to each tube.
4. Vortex for 1-2 seconds at a low setting.
5. Place one Ventre-Sep ® Ferritin Antibody Stick in each tube so that it rests on the notch. Press all sticks into tubes as rapidly as possible.
6. Incubate for 60 minutes at room temperature.
7. Invert tubes and gently shake up and down to drain. Blot on an absorbent pad.
8. Add approximately 2.5 ml of tap water to each tube. Repeat Step 7 (above).
9. Repeat wash and rinse procedure in Step 8 (above).
10. Add 1.0 ml Ferritin Buffered Tracer Reagent to each tube.
11. Incubate for one hour at room temperature.
12. Invert tubes and gently shake up and down to drain into radioactive waste container; blot on an absorbent pad.
13. Rinse each tube with approximately 2.5 ml 0.01% Triton. Repeat Step 12 (above).
14. Repeat wash and rinse procedure in Step 13 (above).
15. Place tubes in gamma scintillation counter and count.

Figure 6:
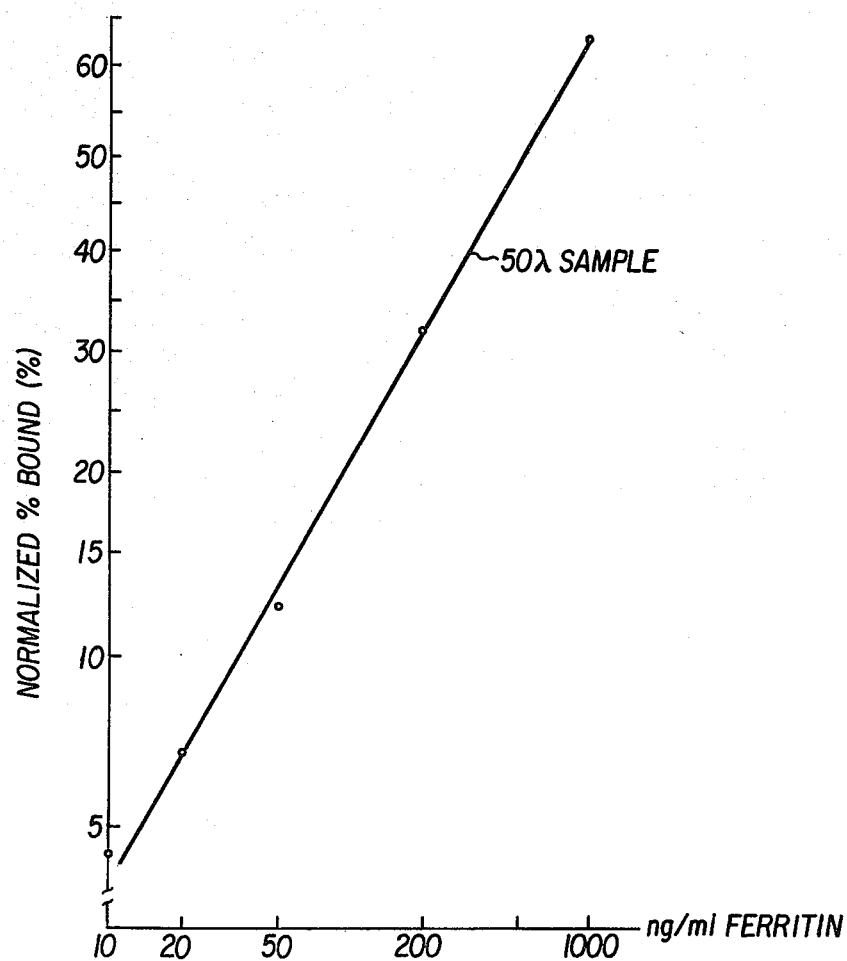

The assay buffer consists of phosphate-buffered saline. The Ferritin buffered tracer reagent was prepared by adding $^{125}$I-labeled anti-Ferritin to PBS. Sufficient labeled anti-Ferritin was added to the buffer to provide approximately 250,000 cpm/ml of buffer. Fifty microliters of standard containing 5, 10, 20, 50, 200, 500, 1,000, 20,000, or 75,000 nanograms/ml were added to the appropriate tube. In addition, two controls were also tested. The results are shown in FIG. 6, plotted as the normalized percent bound versus the concentration of Ferritin. The normalized percent bound is calculated by dividing the observed counts per minute by two times the observed counts per minute for the 500 nanograms/ml standard and multiplying this by 100 percent. That is, the normalized percent bound equals:

$$\frac{cpm}{2(cpm \text{ for } 500 \text{ ng/ml std.})} \times 100\%.$$

The Ferritin concentration is plotted on a log scale and the normalized percent bound is plotted on percentage scale. This figure shows that the amount of labeled antibody bound increases with the amount of antigen bound.

The controls which were utilized were prepared by adding a known quantity of Ferritin to human serum. The controls were assayed as described above and the normalized percent bound calculated and the experimental concentration of Ferritin determined from the graph. The following Table shows the theoretical and experimental values in ng/ml.

TABLE 3

| Control | Theoretical | Experimental 50 ul |
|---|---|---|
| 1 | 32 | 26 |
| 2 | 194 | 175 |

The experimental values correspond closely with the theoretical values.

We claim:

1. In a method for conducting a solid phase in vitro immuno-assay wherein a first component is fixed to the surface of a solid phase device and said device with said fixed component on its surface is thereupon placed in contact with a fluid sample containing an unknown quantity of a mobile component reactive with said first component at a rate or to an extent which is measurable as a function of the concentration of said mobile component in said fluid sample, one of the fixed and mobile components is labelled, the solid phase device and fluid sample are held in contact for a given time interval to permit reaction to occur to a desired extent, and the concentration of said mobile component in said fluid sample is then determined based on the amount of said mobile component which reacted with said fixed component during said given time interval, the improvement which comprises shortening said given time interval significantly by contacting said solid phase device and said fluid sample in a receptacle the inner surface of which has said first component also fixed to its surface and then measuring the amount of said mobile component which reacted with fixed component bound to both said solid phase device and said receptacle.

2. The method of claim 1 wherein said fixed component is an antibody, said mobile component is an antigen to said antibody and the reaction between them is binding of said antigen to said antibody.

3. The method of claim 2 wherein said solid phase device is a central rod with a plurality of finlike projections extending outwardly therefrom along a portion of the length of said rod, said finlike projections having outer edges which conform approximately to the inner shape of said receptacle.

4. The method of claim 3 wherein said solid phase device has at least nine of said finlike projections.

5. The method of claim 3 or claim 4 wherein said receptacle is a test tube.

6. The method of any of claims 1, 2, 3 or 4 in which the label is a radiolabel and is attached to said mobile component prior to commencement of the reaction between said fixed and said mobile components.

7. A solid phase reaction apparatus for measuring or detecting a mobile component in a fluid sample, said apparatus comprising:
 (a) a receptacle having an inner surface,
 (b) an insert having a contact surface which is in contact with the fluid sample when inserted therein, and
 (c) a fixed component immobilized on the inner surface of the receptacle and the contact surface of the insert wherein said fixed component is capable of reacting with said mobile component at a rate or to an extent measurable as a function of the concentration of molecules of said mobile component.

8. The apparatus of claim 7 wherein said insert comprises a central rod and a plurality of fin-like projections extending outwardly from said rod along a portion of the length of said rod, said fins having outer edges conforming approximately to the shape of the receptacle.

9. The apparatus of claim 8 wherein said insert has at least nine fins.

10. The apparatus of claims 8 or 9 wherein said receptacle is a test tube.

* * * * *